(12) United States Patent
Greenfield et al.

(10) Patent No.: US 7,018,839 B2
(45) Date of Patent: Mar. 28, 2006

(54) PEPTIDE FROM SOLUBLE FORM OF ACETYLCHOLINESTERASE, ACTIVE AS A CALCIUM CHANNEL MODULATOR

(75) Inventors: Susan Adele Greenfield, Horton-cum-Studley (GB); David John Talbutt Vaux, Abingdon (GB)

(73) Assignee: Synaptica Limited, Oxfordshire (GB)

( * ) Notice: Subject to any disclaimer, the term of this patent is extended or adjusted under 35 U.S.C. 154(b) by 458 days.

(21) Appl. No.: 09/155,076

(22) PCT Filed: Mar. 21, 1997

(86) PCT No.: PCT/GB97/00796

§ 371 (c)(1),
(2), (4) Date: Oct. 23, 1998

(87) PCT Pub. No.: WO97/35962

PCT Pub. Date: Oct. 2, 1997

(65) Prior Publication Data

US 2002/0054870 A1    May 9, 2002

(30) Foreign Application Priority Data

Mar. 22, 1996 (GB) .................................. 9606040

(51) Int. Cl.
*C12N 5/16* (2006.01)
*C12N 5/06* (2006.01)
*A61K 38/00* (2006.01)
*C07K 14/00* (2006.01)
*C07K 16/00* (2006.01)

(52) U.S. Cl. ...................................... 435/326; 530/300
(58) Field of Classification Search ................ 530/300, 530/350, 333; 435/68.1, 69.1; 424/184.1
See application file for complete search history.

(56) References Cited

U.S. PATENT DOCUMENTS 5,932,780 A * 8/1999 Soreq et al.

FOREIGN PATENT DOCUMENTS

EP    0 288 243 A    10/1988

OTHER PUBLICATIONS de Serres et al., Cellular and Molecular Neurobiology, 13(3):279-87, 1993.*
Moran et al., Acta Neuropatthologica 85(4):362-9, 1993.*
Skolnick et al., Trends in Biotech 18(1):34-39, 2000.*
Dagerlind et al., 62(1):217-39, 1994.*
S. Bon et al., "Identical N-terminal peptide sequences of asymmetric forms and of low-salt-Soluble and detergent-soluble amphiphilic dimers of Torpedo acetylcholinesterase". FEBS Letters, vol. 209, No. 2, Dec. 1986, pp. 206-212.
H.I. Ziltener et al., "Monoclonal antipeptide antibodies recognize IL-3 and neutralize its bioactivity in vivo", Journal of Immunology, vol. 140, No. 4, Feb. 15, 1998, Baltimore US, pp. 1182-1187.
T.L. Leto et al., "Characterization of the calmodulin-binding site of nonerythroid α-spectrin". The Journal of Biological Chemistry, vol. 264, No. 10, Apr. 5, 1989, MD US, pp. 5826-5830.
Chemical Abstracts, vol. 118, No. 23, Jun. 7, 1993, Columbus, Ohio, US, Abstract No. 227311, XP002035623 & J. Bacteriology, vol. 174, No. 13, 1992, pp. 4361-4373, J.P. Mueller et al., "Teranscriptional regulation of *Bacillus subtilis* glucose starvation-inducible genes; control of gsiA by the comP-comA transduction systems".
Chemical Abstracts, vol. 121, No. 19, Nov. 7, 1994, Columbus, Ohio, US, Abstract No. 222683, XP002035624 & Neuroscience, vol. 62, No. 1, 1994, Oxford, pp. 217-239, A. Dagerlind et al., "Immunologically induced sympathectomy of preganglion nerves by antibodies against acetylcholinesterase: increased levels of peptides and their messenger RNAs in rat adrenal chromaffin cells".
Chemical Abstracts, vol. 102, No. 25, Jun. 24, 1985, Columbus, Ohio, US; Abstract No. 217461, XP002035625 & J. Neurochem., vol. 44, No. 5, 1985, D.J. Marsh & J. Massoulie: "Proteolytic digestion patterns of soluble and detergent-soluble bovine caudate necleus acetylcholinesterases".
S. Budavari et al., "The Merck Index", 1996, Merck & Co., Whitehouse Station, New Jersey, USA XP002035622 408196.

* cited by examiner

*Primary Examiner*—Sharon Turner
(74) *Attorney, Agent, or Firm*—Wenderoth, Lind & Ponack, L.L.P.

(57) ABSTRACT

The acetylcholinesterase 14-mer peptide AEFHRWSSYM-VHWK acts alone or in synergism with $^2$-amyloid to contribute to neuronal degeneration, e.g. in Parkinson's and Alzheimer's diseases, perhaps by exerting calcium channel opening activity. Antibodies and other compounds which inhibit the biological activity are useful for prophylaxis or treatment.

5 Claims, 1 Drawing Sheet

Fig.1.

```
Hum AChE   ------------LSATDTLDEAERQWKAEFHRWSSYMVHWKNQF----DHY-S
Rab AChE   AFWNRFLPKLLSATDTLDEAERQWKAEFHRWSSYMVHWKNQF----DHY-S
Mus AChE   ------------LSATDTLDEAERQWKAEFHRWSSYMVHWKNQF----DHY-S
Rat AChE   ------------LSATDTLDEAERQWKAEFHRWSSYMVHWKNQF----DHY-S
Bov AChE   -FWNRFLPKLLNATDTLDEAERQWKAEFHRWSSYMVHWKNQF----DHY-S
Hum BChE   ------------TGNIDEAEWEWKAGFHRWNNYMNDWKNNF----NDYTS
Rab BChE   ------------KVLEMTGNIDEAEQEWKAGFHRWNNYMNAWKNNF----NDYTS
Mus BChE   ------------MTGDIDETEQEWKAGFHRWSNYMNDWQNQF----NDYTS
Hum Amy1   ------SGLTNIKTEEISEYKMDAEFRHDSGYEVHHQKLVFFAEDVGS

Hum AChE   KQDRCSDL*------------------------  (SEQ ID NO: 6)
Rab AChE   KQDRCSDL*------------------------  (SEQ ID NO: 7)
Mus AChE   KQERCSDL*------------------------  (SEQ ID NO: 8)
Rat AChE   KQERCSDL*------------------------  (SEQ ID NO: 9)
Bov AChE   KQDRCSDL*------------------------  (SEQ ID NO: 10)
Hum BChE   KKESCVGL*------------------------  (SEQ ID NO: 11)
Rab BChE   KKERCAGF*------------------------  (SEQ ID NO: 12)
Mus BChE   KKESCTAL*------------------------  (SEQ ID NO: 13)
Hum Amy1   NKGAIIGLMVGGVVIATVIVITLVMLKK      (SEQ ID NO: 14)
``` ved rapidly. According to the invention, antagonists of the non-cholinergic action of AChE are expected to be of interest in the prophylaxis and treatment of cancer.

SEQUENCE LISTING

```
<160> NUMBER OF SEQ ID NOS: 15

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: PEPTIDE

<400> SEQUENCE: 1

Ala Glu Phe His Arg Trp Ser Ser Tyr Met Val His Trp Lys
  1               5                  10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: PEPTIDE

<400> SEQUENCE: 2

Asp Ala Glu Phe Arg His Asp Ser Gly Tyr Glu Val His His Gln Lys
  1               5                  10                  15

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: PEPTIDE

<400> SEQUENCE: 3

Tyr Met Val His
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: PEPTIDE

<400> SEQUENCE: 4

Met Val His Trp
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: PEPTIDE

<400> SEQUENCE: 5
```

Val His Trp Lys
 1

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 6

Leu Ser Ala Thr Asp Thr Leu Asp Glu Ala Glu Arg Gln Trp Lys Ala
 1               5                  10                  15

Glu Phe His Arg Trp Ser Ser Tyr Met Val His Trp Lys Asn Gln Phe
            20                  25                  30

Asp His Tyr Ser Lys Gln Asp Arg Cys Ser Asp Leu
        35                  40

<210> SEQ ID NO 7
<211> LENGTH: 54
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 7

Ala Phe Trp Asn Arg Phe Leu Pro Lys Leu Leu Ser Ala Thr Asp Thr
 1               5                  10                  15

Leu Asp Glu Ala Glu Arg Gln Trp Lys Ala Glu Phe His Arg Trp Ser
            20                  25                  30

Ser Tyr Met Val His Trp Lys Asn Gln Phe Asp His Tyr Ser Lys Gln
        35                  40                  45

Asp Arg Cys Ser Asp Leu
    50

<210> SEQ ID NO 8
<211> LENGTH: 44
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 8

Leu Ser Ala Thr Asp Thr Leu Asp Glu Ala Glu Arg Gln Trp Lys Ala
 1               5                  10                  15

Glu Phe His Arg Trp Ser Ser Tyr Met Val His Trp Lys Asn Gln Phe
            20                  25                  30

Asp His Tyr Ser Lys Gln Glu Arg Cys Ser Asp Leu
        35                  40

<210> SEQ ID NO 9
<211> LENGTH: 44
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 9

Leu Ser Ala Thr Asp Thr Leu Asp Glu Ala Glu Arg Gln Trp Lys Ala
 1               5                  10                  15

Glu Phe His Arg Trp Ser Ser Tyr Met Val His Trp Lys Asn Gln Phe
            20                  25                  30

```
Asp His Tyr Ser Lys Gln Glu Arg Cys Ser Asp Leu
        35                  40

<210> SEQ ID NO 10
<211> LENGTH: 53
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 10

Phe Trp Asn Arg Phe Leu Pro Lys Leu Leu Asn Ala Thr Asp Thr Leu
 1               5                  10                  15

Asp Glu Ala Glu Arg Gln Trp Lys Ala Glu Phe His Arg Trp Ser Ser
                20                  25                  30

Tyr Met Val His Trp Lys Asn Gln Phe Asp His Tyr Ser Lys Gln Asp
            35                  40                  45

Arg Cys Ser Asp Leu
        50

<210> SEQ ID NO 11
<211> LENGTH: 42
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 11

Thr Gly Asn Ile Asp Glu Ala Glu Trp Glu Trp Lys Ala Gly Phe His
 1               5                  10                  15

Arg Trp Asn Asn Tyr Met Asn Asp Trp Lys Asn Gln Phe Asn Asp Tyr
                20                  25                  30

Thr Ser Lys Lys Glu Ser Cys Val Gly Leu
            35                  40

<210> SEQ ID NO 12
<211> LENGTH: 47
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 12

Lys Val Leu Glu Met Thr Gly Asn Ile Asp Glu Ala Glu Gln Glu Trp
 1               5                  10                  15

Lys Ala Gly Phe His Arg Trp Asn Asn Tyr Met Asn Ala Trp Lys Asn
                20                  25                  30

Asn Phe Asn Asp Tyr Thr Ser Lys Lys Glu Arg Cys Ala Gly Phe
            35                  40                  45

<210> SEQ ID NO 13
<211> LENGTH: 43
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 13

Met Thr Gly Asp Ile Asp Glu Thr Glu Gln Glu Trp Lys Ala Gly Phe
 1               5                  10                  15

His Arg Trp Ser Asn Tyr Met Asn Asp Trp Gln Asn Gln Phe Asn Asp
                20                  25                  30
```

-continued

```
Tyr Thr Ser Lys Lys Glu Ser Cys Thr Ala Leu
            35                  40

<210> SEQ ID NO 14
<211> LENGTH: 70
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 14

Ser Gly Leu Thr Asn Ile Lys Thr Glu Glu Ile Ser Glu Tyr Lys Met
 1               5                  10                  15

Asp Ala Glu Phe Arg His Asp Ser Gly Tyr Glu Val His His Gln Lys
            20                  25                  30

Leu Val Phe Phe Ala Glu Asp Val Gly Ser Asn Lys Gly Ala Ile Ile
        35                  40                  45

Gly Leu Met Val Gly Gly Val Val Ile Ala Thr Val Ile Val Ile Thr
    50                  55                  60

Leu Val Met Leu Lys Lys
 65                  70

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: POLYPEPTIDE

<400> SEQUENCE: 15

Ala Gly Phe His Arg Trp Asn Asn Tyr Met Met Asp Trp Lys
 1               5                  10
```

PEPTIDE FROM SOLUBLE FORM OF ACETYLCHOLINESTERASE, ACTIVE AS A CALCIUM CHANNEL MODULATOR

BACKGROUND OF THE INVENTION

1. Field of the Invention

This invention concerns the enzyme acetylcholinesterase (AChE) in which the inventors have identified a biologically active peptide.

2. Description of the Related

The classical or cholinergic role of AChE is to degrade enzymatically extracellular acetylcholine. However, it has long been known that AChE exists also in a soluble form, (not a requirement for its classic enzymatic role) and is found in parts of the body where there is little or no acetylcholine. It is becoming widely accepted that AChE has a non-cholinergic function, though the biochemical basis for this function remains unclear.

It is believed that excessive AChE may enhance calcium entry into cells independent of its normal enzymatic action. Elevated cellular calcium levels may lead to a range of pernicious consequences, including undesirable changes in gene expression and, more importantly, mitochondrial swelling which may thereby compromise ATP metabolism and may indeed lead to apoptosis or programmed cell-death. Disease states which may be implicated include Parkinson's disease, Alzheimer's disease, stroke and malignancy.

The cytoplasm of cells typically contains calcium at concentrations of the order of 1 μm. Calcium is present intracellularly in the endoplasmic reticulum in millimolar concentrations. Extracellular body fluids contain calcium also in millimolar concentrations. A calcium pump operates to maintain this substantial concentration difference between the cytoplasm and the endoplasmic reticulum, and thapsigargin is known to be implicated in the breakdown of this pump. Similarly a calcium pump normally functions between the cytoplasm and the extracellular fluid. It is believed that the consequences of the action of excessive AChE may be comparable to the breakdown of these pumps.

AChE, acting in a non-cholinergic capacity, has been shown to play an important part in the normal and abnormal functioning of the substantia nigra, the region affected in Parkinson's disease. There are are three possible ways in which AChE may have toxic effects:

(i) excessive AChE may be released as a consequence of compensatory mechanisms known to occur in that disorder;

(ii) excessive glutamatergic activity known to occur in Parkinson's disease may lead to over-stimulation of calcium channel N-methyl-D-aspartate (NMDA) glutamate receptors, thereby converting a physiological situation to a pathological one;

(iii) normal levels of AChE may act synergistically with fragments of β-amyloid precursor proteins known to be present in the Parkinsonian substantia nigra.

AChE, again acting in a non-cholinergic capacity, may be an important contributing factor in Alzheimer's disease. In transgenic mice with excessive AChE there are cognitive deficits reminiscent of Alzheimer's disease. Moreover Alzheimer's disease has been directly associated with inappropriate levels and forms of AChE. Excessive AChE may act to enhance calcium entry through overactivation of otherwise normal adaptive processes via a mechanism discussed in the experimental section below.

Current therapies for both degenerative diseases are somewhat inadequate. Anti-Parkinsonian drugs which target dopamine substitution do not arrest neuronal cell loss, and newer drugs aiming to block calcium entry directly may have poor net payoff in terms of neuronal health and in addition would have widespread undesirable effects in both the central nervous system and peripheral tissue. Moreover, drugs used in Alzheimer's disease which exclusively target the cholinergic system, neglect areas where AChE may be having its pivotal non-cholinergic function. Previous attempts to target calcium channel activity in therapy for neurodegenerative disorders have been hampered by the non-selective effects of the compounds available.

In order to be conveniently administered, a compound for treatment of disorders of the central nervous system, or more particularly of the brain, needs to be capable of crossing the blood-brain barrier. AChE is not capable of doing this, though a small lipid-soluble analogue of part of this molecule might be. Workers in the field have been seeking biologically active peptides based on the AChE molecule for more than ten years, in the hope of thereby achieving a more effective and selective treatment for disorders of the central nervous system such as Alzheimer's and Parkinson's diseases.

It is known that antagonism of NMDA receptors is being explored as a therapy for stroke. The present invention is expected to find application in specific therapies for combating stroke and other problems of cerebral circulation.

Abnormal cholinesterase expression occurs in several types of tumour cells. Although the role of cholinesterases in tumorigenesis is unclear, the fact that AChE and BuChE (butyryl cholinesterase) may be involved in the control of cell growth and proliferation during early development suggests that the amplification of cholinesterase genes may influence the ability of tumour cells to proliferate more rapidly. According to the invention, antagonists of the non-cholinergic action of AChE are expected to be of interest in the prophylaxis and treatment of cancer.

Several separate lines of evidence suggest that motor neurones may share, along with the neurones that are lost in Parkinson's disease (substantial nigra) and in Alzheimer's disease (basal forebrain, locus courulues, raphe nucleus) several distinctive features as well as the common characteristic of releasing AChE in a non-cholinergic capacity. The released AChE may have a novel action, as in the regions prone to Parkinsonian or Alzheimer degeneration to enhance developmental mechanisms in immature populations of motor neurones but exert toxic actions if inappropriately reactivated in mature systems. The AChE-peptide described herein may also therefore be pivotal in the aetiology of Motor Neurone Disease. The undisclosed finding supporting this claim is that in pilot studies, the AChE peptide binds bilaterally to selective sites within the spinal cord.

Amyloid precursor protein (APP) is known to have similar features to AChE as follows. Both AChE and APP are secreted from neurons into the cerebro spinal fluid (CSF), where for both AChE and APP there is a decrease in CSF levels in Alzheimer's disease. Both AChE and APP can have trophic functions.

Both AChE and β-amyloid enhance calcium entry through NMDA receptors. Both AChE and APP activate potassium channels, probably linked to changes in intracellular calcium. Both AChE and β-amyloid activate macrophages. Low stimulation of NMDA receptors has trophic effects whereas high stimulation is toxic. The dual trophic-toxic action of both APP and AChE may thus be mediated via NMDA receptors. A similar dual action via NMDA receptors has already been shown for the trophic factor BDNF in cortical cells. Finally, β-amyloid and the monomer of AChE can bind together as a complex.

This invention results from the inventors' identification of a region of the AChE molecule from which a biologically active peptide (obtained either synthetically or by endogenous processing) can be derived. The peptide consists of 14 residues of AChE from residue 535 to residue 548 of the mature protein (in the translation of the mRNA sequence, EMBL accession hsache. empri, number M55040, beginning at nucleotide 310). The sequence of this peptide is amino Ala-Glu-Phe-His-Arg-Trp-Ser-Ser-Tyr-Met-Val-His-Trp-Lys-carboxy (SEQ. ID No: 1), or in the one letter code, AEFHRWSSYMVHWK. The inventors propose that this, or a related, peptide from this region of AChE acts alone or in synergism with a fragment of beta-amyloid to contribute to neuronal degeneration. The invention thus provides in one aspect a peptide containing at least six amino acid residues and having at least 70% homology with part or all of the above sequence. Preferably the peptide contains at least 12 amino acid residues having at least 90% homology with the above sequence.

BRIEF DESCRIPTION OF THE DRAWINGS

FIG. 1 depicts multiple sequence alignments of five AChE sequences, three BuChE sequences and the human amyloid precursor polypeptide at the region of interest. Specifically, it depicts an alignment of polypeptide sequences of hum AChE (human AChE; SEQ ID NO: 6), rab AChE (rabbit AChE; SEQ ID NO: 7), mus AChE (mouse AChE; SEQ ID NO: 8), rat AChE (rat AChE; SEQ ID NO: 9), Bov AChE (bovine AChE; SEQ ID NO: 10), hum BuChE (human BuChE SEQ ID NO: 11), rab BuChE (rabbit BuChE; SEQ ID NO: 12), mus BuChE (mouse BuChE; SEQ ID NO: 13) and hum Amyl (human A4 amyloid precursor polypeptide: SEQ ID NO: 14). Residues in bold are conserved across all sequences. Boxed residues are shared by all AChEs and hum Amyl but none of the BuChE sequences. Amyloid peptide residues 1–42 are shown within a box. The bar above the alignment indicates the position of the AChE and BuChE synthetic peptides, while the bar below the alignment identifies the synthetic APP peptide.

It appears that the two amino acid residues-Val-His-, appearing at positions 11 and 12 in the above sequence, may be of critical importance. Thus the invention also envisages peptides comprising or consisting of the four-mer sequence YMVH (SEQ. ID No: 3) or MVHW (SEQ. ID No: 4) or VHWK (SEQ. ID No: 5) and having at least 70% homology with part or all of the above AChE sequence.

A somewhat similar peptide is present in a region of the β-amyloid precursor polypeptide. This region lies at the amino terminus of the 42 residue peptide that accumulates in Alzheimer's disease and has the sequence amino -Asp-Ala-Glu-Phe-Arg-His-Asp-Ser-Gly-Tyr -Glu-Val-His-His-Gln-Lys-carboxy (SEQ. ID No: 2), or in the one letter code, DAEFRHDSGYEVHHQK, corresponding to residues 597–612 of the translation of the human amyloid A4 precursor polypeptide (EMBL accession hsafpa4. empri number Y00264, beginning at nucleotide 148).

The accompanying table shows the multiple sequence alignment of 5 AChE sequences, three BuChE sequences and the human amyloid precursor polypeptide at the region of interest. As reported in the experimental section below, the human amyloid precursor fragment does not itself exert calcium channel opening activity, but it does enhance the activity of the AChE fragment. The BuChE fragment appears inactive, both alone and together with the AChE fragment. In another aspect the invention thus envisages a mixture of AChE peptide with another peptide having at least four amino acid residues preferably including VH and having at least 70% homology with the above β-amyloid precursor sequence.

There are various ways in which this AChE peptide or this peptide mixture may be used:

a) Since the AChE peptide is shown to have nanomolar affinity for a binding site in the vulnerable cells, the peptide (or mixture) can be labelled with a signal moiety, or alternatively immobilised, and used to locate and identify the receptor site of the cells. The nature of this signal moiety is not material, and the technique of labelling peptides with signal moieties is well known. The peptide (or mixture) can be used as an affinity ligand for the selective retrieval of the receptor molecule itself from preparations derived from those vulnerable cells. Additionally, the peptide affinity ligand could be used to screen an appropriate cDNA expression library to isolate a cDNA encoding the binding site directly. Once that receptor site is known, it will be possible to modify or control its properties.

b) An alternative and preferred approach is to find a substance that inhibits the action of the biologically active peptide or mixture. For example an antibody or other substance which binds to the peptide would be expected to inhibit its biological action. Structural properties of the active peptide itself, together with a combinatorial analysis of the optimal peptide sequence for biological activity, will provide additional information. This structural information may suggest a family of synthetic (non-peptide) compounds that could rationally be tested for efficacy.

In a further aspect, the invention thus envisages a compound which inhibits a biological activity of the AChE peptide or peptide mixture described above. The biological activity may perhaps be modulating, directly or indirectly a calcium-channel-opening activity. The compound will preferably be capable of crossing the blood-brain barrier.

Thus the non-cholinergic action of AChE, as mimicked by its 14 residue peptide, may be selectively blocked by a synthetic compound devised in this way. Moreover, the process of developing such a synthetic inhibitor is simplified by the demonstration of biological activity in such a small sub-fragment of the AChE molecule. A consequence should be that the synthetic compound offers a more physiological action, thus reduction of calcium entry into vulnerable cells rather than complete abolition. In addition, this action should occur selectively, only in locations within the brain where AChE has a non-cholinergic action. It should be noted that these are the very sites primarily affected by cell loss in Alzheimer's and Parkinson's diseases. Thus use of these synthetic compounds should avoid widespread disruption of cellular calcium regulation, by offering a highly region-selective action within the brain.

EXAMPLE 1

Strategy for the Identification of a Receptor for the AChE Peptide

1. Use the peptide, tagged with biotin, to search for a cell type with a high affinity binding site for the peptide. Note that this search will begin with neuronal-derived tissue culture cell lines that should be good candidates. Functional significance for the binding of the AChE peptide will be assessed by looking for physiological effects of peptide binding, such as transient calcium currents.

2. Having identified a cell type with a high affinity binding site for the peptide, the receptor will be identified by ligand overlay blotting and intracellular localisation by indirect detection of the biotinylated peptide using a streptavidin conjugated fluorochrome. Subsequently the receptor will be purified either by affinity chromatography using immobilised peptide, or by conventional column chromatography using the ability of the peptide to bind to column fractions as an assay to follow purification.

3. The purified receptor will be subject to N-terminal microsequencing (or tryptic fragments will be purified by HPLC and microsequenced if the receptor molecule as isolated proves to be N-terminally blocked). The peptide sequences obtained in this way will be compared with a non-redundant compilation of available peptide sequence databases to identify any similarities (or identity with a known surface molecule). The sequences will also be compared with expressed sequence tag (EST) databases in case the mRNA for the receptor has already been obtained as a cDNA by chance in a random library construction and sequencing project.

4. If the strategy in (3) does not identify a cDNA sequence, the peptide sequences will be back-translated to provide nucleotide sequences from which oligonucleotides will be constructed. These oligonucleotides will be used to amplify regions of the parent mRNA by reverse transcription of total cellular RNA (from the cell type used in the original biochemical isolation), followed by specific amplification with each possible primer pair using the polymerase chain reaction (PCR). These PCR products will be directly sequenced by cycle sequencing using an Applied Biosystems automated sequencer.

5. The sequences obtained from these PCR products will be compared with sequences in existing nucleotide databases as in. (3). If this comparison reveals that an identical sequence has previously been obtained, then a strong candidate for the receptor gene is available (Note that this does not imply that the sequence that has been obtained previously has already been implicated in any way in the functions that the invention ascribes to this molecule).

6. If no identical or highly similar sequences are identified in (5), then the PCR-derived nucleotide fragments will be used as radiolabelled probes to screen a cDNA library constructed by oligo-dT primed reverse transcription from the mRNA of the cell type used in the original biochemical isolation. This will identify candidate cDNA clones which will then be sequenced as above. The identity of the candidate cDNAs with the protein of interest will be confirmed initially by demonstrating that the clone contains the sequences of the other PCR-derived nucleotide fragments. If an incomplete cDNA clone is obtained then 5' extension will be carried out using the RACE technique (Rapid amplification of cDNA ends).

7. The function of the protein encoded by the cDNA will be confirmed by expression of the full-length protein using a transient eukaryotic expression vector in cells previously shown not to have a high affinity binding site for the AChE peptide. Expression of the protein in these cells should result in the appearance of a high affinity binding site for the AChE peptide on these transfected cells. This will confirm that the correct sequence has been identified.

8. The cDNA sequence will be used to express the protein in a baculovirus-infected insect cell system in order to obtain large amounts of pure protein for structural studies. Note that this may require the construction of a soluble ectodomain fragment if the protein is a transmembrane molecule. The structural studies will include circular dichroism (CD) measurements, 2-D nuclear magnetic resonance analysis (NMR) and attempts at crystallisation. Pure receptor protein will also facilitate detailed analysis of the binding of peptides, or candidate non-peptide agonists (or antagonists), to the receptor using surface plasmon resonance methods.

9. Once the AChE ligand and its receptor are known, there are various ways of controlling or preventing their action:

a) Destroy the ligand, i.e. identify a protease that cleaves the active peptide ligand into an inactive form and promote its activity e.g. by inducing it or impregnating it.

b) Prevent production of the ligand, i.e. identify a protease that produces the ligand and inhibit that.

c) Sequester the ligand and remove it with antibody or with soluble receptor ectodomain. A modification of this approach is possible if the AChE/β-amyloid synergy results from competition for a high affinity sequestration site different from that which produces the biological effect. Introduction of excess of high affinity site will reduce the biological effect.

d) Block the receptor with an antagonist, e.g. design an analogue that binds the receptor, competes with endogenous peptide, but does not raise calcium levels. In an experimental system showing binding and calcium ion signals, it will be possible to assay for a class of compounds that bind the receptor, compete with the peptide ligand, but do not themselves activate the receptor.

e) Uncouple the receptor from the cellular response, e.g. by preventing ligand binding to the receptor from causing cellular response by blocking a second messenger that is preferably unique to the system.

EXAMPLE 2

The 14-mer AChE peptide, the corresponding 14-mer human BuChE peptide (AGFHRWNNYMMDWK) (SEQ. ID No: 15)and the 16-mer β-amyloid peptide were synthesised and used in studies to assess their biological activity, with the summarised results given in Examples 3 to 7

EXAMPLE 3

(i) Electrophysiological Studies

These experiments are performed on slices of guinea-pig midbrain maintained in vitro. Intracellular recordings are made from a rostral population of neurons in the substantia nigra under current clamp conditions. All results listed below are obtained in the presence of the sodium channel blocker tetrodotoxin. In order to facilitate visualisation of calcium-mediated potentials triggered by activation of NMDA receptors, all experiments are performed in magnesium-free perfusate. Under these conditions, results to date indicate:

(a) In 11 neurons, in concentrations ranging from $10^{-7}$M to $10^{-6}$M, the peptide fragment derived from AChE has a selective and reversible action reminiscent of the actions of AChE itself, i.e. with lower doses/less sensitive situations there is an enhanced calcium influx. This effect is followed by, in sustained applications/stronger doses/more sensitive neurons, a marked reduction in the calcium potentials.

(b) Under conditions where AChE is normally effective and under magnesium-free conditions, the comparable BuChE fragment appears without corresponding effect (n=3), and the analogous fragment of β-amyloid also appears ineffective (n=4). However, a synergism between the peptide derived from AChE and this fragment of β-amyloid is reflected in a reduction in the evoked calcium potential (n=7) followed by the generation of large spontaneous thapsigargin-sensitive calcium currents oscillating in a biphasic manner (n=3).

(c) In 6 neurons, application of NMDA, which on its own produces a 'physiological' depolarisation, results, under identical conditions, in severe metabolic stress of the cell after treatment with the AChE peptide at a concentration as low as $10^{-7}$M, or at an even lower concentration when combined with the amyloid peptide.

High doses of NMDA, repeated electrical stimulation and indeed raised extra cellular calcium levels, all result in an effect on calcium potentials similar to that seen for AChE peptide. The most obvious common factor in these three other treatments is that all to them enhance calcium entry; the most parsimonious explanation for the reduction in calcium potential, seen following AChE peptide, is that the peptide enhances calcium entry too.

These results suggest that the peptide specified in the invention is enhancing calcium entry into a population of neurons in the substantia nigra. Once large amounts of calcium have entered the neuron, buffering mechanisms come into play, reflected by the marked reduction in calcium potential. At its most effective, when the peptide is combined with the fragment from β-amyloid, then this enhanced calcium entry followed by the triggering of intracellular control mechanisms, is seen as a spontaneous oscillation. It has already been shown that recombinant AChE, acting in a non-classical fashion, can enhance calcium entry into these neurons via a modulatory action on the NMDA receptor. These results suggest that the peptide derived from AChE, specified in the invention, could be responsible for this effect.

(ii) Behavioural Studies

In these experiments, rats were chronically implanted with a cannula in one substantia nigra and left to recover. After a period of about 3 days, they were infused with either a saline control solution, or a solution containing the 14-mer AChE peptide of the invention at a dose of 1 μl of $10^{-5}$M. After a single infusion, they were challenged daily with a systemic application of amphetamine for the subsequent 10 days. Although the control group (n=6) showed no significant effects, the group receiving the peptide (n=8) gradually started to display contraversive rotation, which reached a maximum after 7 days post infusion and remained consistent for the remaining 3 days tested.

These results suggest that the peptide-mediated calcium entry observed in (i) could be setting in train long-latency, long-term intracellular events that result in a sustained elevation of the activity of neurons in the treated substantia nigra. This enhanced, unilateral activation is manifest as contraversive circling behaviour.

AChE when infused unilaterally into the substantia nigra produces a long-term increase in circling behaviour which reflects increased activity of the nigrostriatal pathway. Under some circumstance this effect is mimicked by AChE-peptide, although the onset of the effect takes several days following peptide infusion and the response is variable. A low concentration of APP-peptide also increases activity of the nigrostriatal pathway, although doubling the concentration reverses this effect, possibly reflecting the change from trophic to toxic actions of this agent. AChE- and APP-peptide appear to interact.

EXAMPLE 4

Electrophysiological Evidence for an Effect of the AChE 14-mer Peptide on Neurones of the Hippocampus The hippocampus is a brain region remote from the substantia nigra detailed in the original application. This issue is important because an effect of the peptide in the substantia nigra can be connected to Parkinson's disease because cells in the substantia nigra are lost during the development of this condition. By contrast an effect in the hippocampus can be connected to Alzheimer's disease because the hippocampus is a major site of degenerative neuropathology in Alzheimer's disease.

Data has been obtained to suggest that the peptide has direct toxic effects on hippocampal cells in organotypic cultures. The effect is synergistic with the known excitotoxic effects of N-methyl-D-aspartate (NMDA), can be seen within one hour of application. Toxic effects are also detectable histochemically over a culture period of three weeks. This is particularly important because there is a need for a demonstration of peptide toxicity in a system related to a major neurodegenerative disorder.

The organotype tissue culture technique requires postnatal (day 5–7) rats given terminal anaesthesia followed by decapitation. Sections of hippocampus, 400 μm thick, are prepared and then plated on a plasma/thrombin clot. A serum-based media is added to these cultures, which can then be maintained at constant temperature (35° C.) for up to 21 days. After each study, cultures are stained with trypan blue to assess cell viability, in addition, after every removal of serum media, cultures are assayed for lactate dehydrogenase (LDH—a soluble cytoplasmic enzyme used as an index of cellular damage).

Semi-acute application of the AChE-peptide and/or N-methy-D-aspartate (NMDA) for 1 hour results in extensive cellular damage in various regions of hippocampal sections, compared to control samples.

Following chronic studies (cultures are maintained for 21 days and treated with AChE-peptide and/or NMDA every 3–4 days), cultured cells are immunocytochemically stained for acetylcholinesterase in order to assess what action, if any, the AChE-peptide has on cell number. The findings of biochemical studies (LDH assays) carried out on these chronic cultures support the proposed toxic action of AChE-peptide following its semi-acute application to hippocampal sections. However, current work suggests that acetylcholinesterase-positive cells may be protected to some extent and, therefore it is possible that either acetylcholinesterase-negative cells are selectively vulnerable or the AChE-peptide may have a more pronounced action when applied with NMDA or both these cases may apply.

EXAMPLE 5

Reproducible Binding of Peptide to Brain Sections

In order to obtain a probe derived from the AChE-peptide that could be followed when bound to specific sites within sections of brain (whether rodent or human) a modified peptide was made. The modified peptide consisted of the AChE-peptide to which was covalently attached at the N terminus a fluorescein group. This modified peptide was bound to fixed permeabilised brain sections, the excess unbound material washed off and then the fluorescein group detected with an alkaline phosphatase conjugated monoclonal anti-fluorescein reagent. This in turn was washed to remove the unbound excess, and a substrate that produces a highly localised, coloured, insoluble precipitate in the presence of alkaline phosphatase was added in a solution of pH 8.4. Finally, the reaction was stopped by lowering the pH to neutral (pH 7.0) and the distribution of the reaction product was examined by microscopy and photography.

This indirect ligand overlay method provides a significant amplification of the weak signal due to peptide binding and overcomes a general problem of background due to non-specific sticking of first or second reagents. A control with the modified peptide omitted was always included, and a drug, levamisole, was routinely used to block the activity of alkaline phosphatase enzymes that are present naturally in the tissue. The result is a clean assay that shows peptide-dependent binding reactions confined to certain brain regions and certain populations of cells within those regions.

The specific example of the cerebellum is a good one; the peptide specifically labels a population of cells with neuronal morphology within the granular cell layer of the cerebellum in rats, guinea pigs and humans. The cells labelled represent a subpopulation of the cells present in this highly cellular layer. In rodents the staining is present in cell bodies, but excluded from the nucleus, and extends into long processes, some of which extend into the molecular cell layer, forming a net around the Purkinje cells, which are themselves negative.

EXAMPLE 6

AChE 14-mer Peptide

Rabbits were immunised by conventional protocols with adjuvant containing a modified AChE-peptide. In this case, the modification was to construct a covalent cluster of four copies of the AChE-peptide connected via three lysine residues. This structure is known as a multi-antennary peptide, or MAP-peptide, and is known to give rise to more potent stimulation of the recipient's immune response in many cases. The rabbits were repeatedly immunised and test bleeds were used to follow the development of a response to the antigen.

The resulting antiserum is a high titre polycolonal antiserum with marked specificity for the AChE-peptide; although the MAP-AChE peptide is recognised with the highest affinity, the reagent is still a potent for binding monomeric AChE-peptide alone. The anti-AChE reactivity is of the IgG subclass, indicating that a secondary response has occurred in the animals.

A skilled reader knows that a similar immunisation protocol in mice (giving the MAP-peptide in an adjuvant into the peritoneal cavity on a number of occasions) would give rise to an immune response to the AChE peptide in mice. This immune response could be immortalised by fusion of immunocompetent cells from the immunised mice (conventionally the spleen but in principle lymph node also) with a nonsecreting myeloma cell line using fusogens such as polyethylene glycol or electrical discharges. Immortalised cell lines producing a reactivity of interest are derived clonally by screening assays based upon the solid phase binding assay used to study the binding of the polyclonal antibody to the peptide. The cells of interest are subcloned to purity, so their product is a single immunoglobulin species and the resulting pure hybridoma population is preserved by freezing in liquid nitrogen and used to produce the monoclonal antibody that is then used in all of the ways that a skilled reader knows of for such reagents.

It is routinely possible to obtain the sequence of the variable regions of the immunoglobulins produced by hybridomas selected in this way. This would be done (as in previously published protocols for other unrelated monoclonal antibodies) by using the polymerase chain reaction to amplify and clone the variable region sequences from messenger RNA isolated from the hybridomas of interest. These regions are then cloned back into a recombinant background that permits the engineering of their association with specific detecting enzymes or prosthetic groups for detection or purification. The recombinant protein is produced in bacteria, or in insect cells using the baculovirus expression system, or in mammalian cell lines.

EXAMPLE 7

Competition Assay

In order to be sure that the antibody recognition of peptides occurs without the possible distortion due to the binding of the peptide to a charged plastic surface, an assay was used in which the critical interaction is studied in solution. Briefly, a solid phase assay was set up using the AChE-peptide on a plastic surface in a small well and an amount of the antibody which will give a large signal of known size when assayed in this solid phase assay. An aliquot of the antibody was preincubated with potential competitors for binding to the AChE-peptide before presenting the resulting mixture to the peptide bound to the well. If the competitor has bound to the anti-peptide antibody during the preincubation, then there will be less free antibody available to bind to the immobilised peptide in the well, and the signal that recorded in the solid phase assay will be reduced.

This assay was first validated by demonstrating that the AChE-peptide itself could compete in this assay in a dose-dependent manner, and was then used to show that the antiserum generated is specific for AChE-peptide. This latter conclusion is drawn from the fact that even excessive doses of the APP or BuChE peptide could not compete for the binding of antibody to immobilised AChE-peptide.

When human CSF was used as the competitor during the preincubation, high levels of competition were recorded showing that human CSF contains a component that is structurally similar to the epitope(s) present in the AChE-peptide.

The Western blotting assay in which the proteins of the CSF are electrophoretically separated according to size and then transferred to a nitrocellulose substrate addresses the question of the identity of the species in human CSF that is recognised by the anti-peptide antiserum. The array of proteins on the nitrocellulose sheet (or blot) is probed with the anti-peptide antibody followed by a secondary antibody covalently attached to alkaline phosphatase. When this assay is performed the anti AChE-peptide antiserum is found to specifically decorate a protein component at approximately 25,000 Dalton molecular mass. This is not the size of the AChE. The protein is present in all CSF samples from both normal and Alzheimer's disease patients.

When the complex antiserum is affinity purified using the 25,000 Dalton protein as the ligand, the resulting antibody recognises the 25,000 Dalton protein as expected, but also a second, apparently less abundant, protein. This second reactivity has the interesting and potentially important property that the size of the protein is smaller in Alzheimer disease patients than in normal controls. Although the number of samples so far looked at is small (3 AD and 3 normal), the effect is completely consistent, so perhaps this is a reproducible difference between the CSF of normal and AD patients. If this is confirmed, the potential for a diagnostic test is clear.

Peptide Length

The inventors have so far only studied one AChE 14-mer peptide length; the evidence that polypeptides of other sizes may contain the functional region is that the anti-peptide antiserum recognises a species of 25,000 Daltons (much larger than the c2,000 Daltons of the AChE-peptide). Furthermore recombinant AChE that contains the part of the protein encoded by exon 6 is an effective competitor in the above competition assay, showing that the region is still recognised by the antibody when it is attached to the parent protein.

Thus, the peptide used may not be uniquely functional because of its size; the functional structure is encoded within the 14-mer, and can be detected by antibody when present in the context of a much larger polypeptide.

The invention claimed is:

1. An isolated peptide consisting of a peptide of SEQ ID No. 1, said peptide having a calcium channel modulatory function.

2. A probe consisting of the peptide of claim 1, labeled with a signal moiety, or immobilized on a solid support.

3. The peptide as claimed in claim 1, which peptide is a fragment of acetylcholinesterase.

4. The peptide as claimed in claim 1, which peptide has been chemically synthesized.

5. A method for obtaining an antibody comprising administering the peptide according to any one of claims 1, 3, and 4 as an antigen to obtain said antibody.

* * * * *